(12) United States Patent
Stein et al.

(10) Patent No.: US 7,988,742 B2
(45) Date of Patent: Aug. 2, 2011

(54) ART WRAP BANDAGE

(76) Inventors: Celeste Ann Stein, Galveston, TX (US);
Ben Jay Stein, Galveston, TX (US)

( * ) Notice: Subject to any disclaimer, the term of this patent is extended or adjusted under 35 U.S.C. 154(b) by 0 days.

(21) Appl. No.: 10/972,503

(22) Filed: Oct. 25, 2004

(65) Prior Publication Data

US 2006/0088686 A1    Apr. 27, 2006

(51) Int. Cl.
*B32B 3/06* (2006.01)
*B41C 1/06* (2006.01)

(52) U.S. Cl. .......... 8/471; 8/445; 8/467; 8/470; 101/33; 101/34; 156/60; 156/230; 428/99

(58) Field of Classification Search ............ 428/99, 428/98, 223; 24/572; 8/471, 445, 467, 470; 101/33, 34; 156/60, 230
See application file for complete search history.

(56) References Cited

U.S. PATENT DOCUMENTS

| | | | | |
|---|---|---|---|---|
| 4,898,592 A | * | 2/1990 | Latzke et al. | 604/307 |
| 5,038,413 A | * | 8/1991 | Ursino | 2/239 |
| 5,912,116 A | * | 6/1999 | Caldwell | 435/5 |
| 2002/0115955 A1 | * | 8/2002 | DeSena | 602/61 |

* cited by examiner

*Primary Examiner* — Brent T O'Hern
(74) *Attorney, Agent, or Firm* — Delphine James

(57) ABSTRACT

The present invention provides a decorative medical covering for the protective wrapping of a skin injury or an orthopedic injury. The decorative medical covering is produced by providing a strip of material of a predetermined length and a predetermined width. The material is composed of a plurality of fibers. An aesthetically pleasing image is stored onto a sublimation transferal medium. The image is transferred from the sublimation transfer medium onto the strip wherein the image is permanently incorporated into the plurality of fibers of the material.

9 Claims, 1 Drawing Sheet

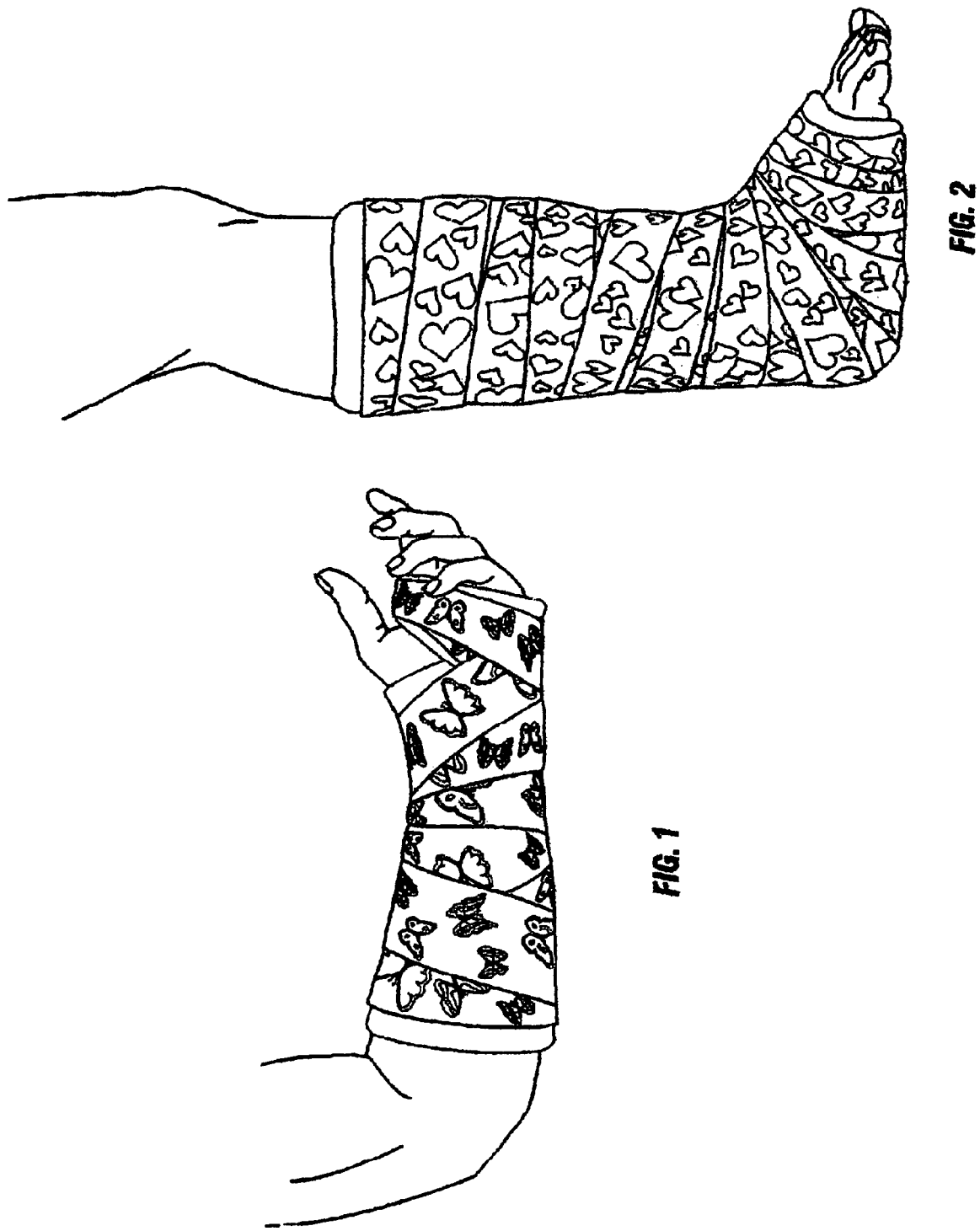

ART WRAP BANDAGE

BACKGROUND

The present invention relates to decorative covers for general or orthopedic injuries. When people have injuries dealing with musculoskeletal system including bones, joints, ligaments, muscles and tendons, physicians utilize specialized mechanical orthopedic devices such as casts, braces, splints or bandages to treat these types of injuries. Normally for serious bone injuries hard casts are utilized, and for sprains bandages are utilized. Additionally, orthopedic mechanical devices as well as normal bandages are not aesthetically pleasing. The present invention alleviates this problem by providing a process and product for decorative covers for orthopedic injuries.

SUMMARY

The present invention provides a decorative medical covering for the protective wrapping of a skin injury or an orthopedic injury. The decorative medical covering is produced by providing a strip of material of a predetermined length and a predetermined width. The material is composed of a plurality of fibers. An aesthetically pleasing image is stored onto a sublimation transferal medium. The image is transferred from the sublimation transfer medium onto the strip wherein the image is permanently incorporated into the plurality of fibers of the material. Sublimation is the process generally used to transfer the image to the fibers of the material. The present invention utilizes the sublimation process to create a new decorative covering for a skin injury or orthopedic injury.

BRIEF DESCRIPTION OF DRAWINGS

FIG. 1 is an illustrative view of the product on a broken arm.

FIG. 2 is an illustrative view of the product on a broken leg.

DETAILED SPECIFICATION

Referring to FIGS. 1 and 2, there is shown a decorative medical covering in accordance with the present invention. FIG. 1 illustrates the decorative covering wrapped around an injured arm, and FIG. 2 illustrates the decorative covering wrapped around an injured leg. The decorative covering can be used independently to cover an injury or can be used as a decorative covering for a cast or another type of orthopedic device.

The decorative covering is produced through the conventional process of sublimation. The decorative covering is for the protective wrapping of a skin injury or an orthopedic injury. The covering comprises a continuous strip of material of a predetermined length and a predetermined width. The material further comprises a plurality of fibers. In the preferred embodiment, the material can be an elastic or non-elastic synthetic material such as polyester. In alternative embodiments, a textured treatment can be applied to the strip material. Additionally, in other embodiments, the material can be made of non-synthetic material as well as tape. However, the sublimation process is normally performed on synthetic materials such as polyester or nylon blends.

An aesthetically pleasing image is stored on a sublimation transfer medium or sublimation paper. The transfer medium is normally a polymer coated transfer paper. The image is transferred from the sublimation transfer medium onto the strip wherein the image is permanently incorporated into fibers of the material. The sublimation process is generally done by heat activation which can be at 400 degrees. The heat causes the image to flash into a gaseous state thereby penetrating and dying the image into the material of the strip. Through the sublimation process, the image becomes part of the material.

In other embodiments of the present invention, at least one decorative object can be attached to the strip at a strategic position. These objects can be removable attached as well as permanently attached. These objects can be gem stones diamonds, pearls, rubies, imitation diamonds, imitation pearls, gold, silver, birthstones, or any other suitable attractive decorative gemstones.

The decorative covering can also be created by printing the image from the computer directly onto the strip of material. Utilizing this process, a sublimation transfer medium is not required. The printer has the capability of performing the sublimation process during printing the image onto the strip of the material whereby the image becomes permanently part of the material which is known as strike-off.

Also, in some embodiments a fastening means can be attached to each opposite of the strip of material so that it can be secured in placed once the strip of material once the injury is fully wrapped. The fastener can be Velcro or another suitable fastening means.

What is claimed is:

1. A method of creating a decorative covering and covering an orthopedic injury that has been covered with a cast comprising:
   providing a strip of material of a predetermined length and a predetermined width for protective wrapping of an injury, the material having a plurality of fibers;
   selecting an aesthetically pleasing decorative image;
   storing the decorative image in a memory of a digital computer;
   transferring the decorative image from the memory onto the strip of material by sublimation by printing wherein heat causes the image to flash into a gaseous state thereby penetrating and dying the image into the material of the strip wherein the decorative image becomes a permanent part of the material to create a decorative covering;
   applying at least one decorative object to the strip wherein the at least one object are gemstones, diamonds, pearls, rubies, imitation diamonds, imitation pearls, gold, silver or birth stones; and
   applying the strip of material to the cast by wrapping the strip of material along a length of the cast wherein the cast is set with a pleasing appearance.

2. The method of claim 1 wherein at least one decorative object is removably attached to at least a predetermined portion of the strip of material.

3. The method of claim 1 wherein the at least one decorative object is gem stones.

4. The method of claim 1 wherein a textured treatment is applied to the strip of material.

5. The method of claim 1 wherein the strip of material is made of a synthetic elastic or non-elastic synthetic material.

6. The method of claim 5 wherein the strip of material is polyester.

7. The method of claim 1 wherein the strip is made of a non-synthetic elastic or non-elastic non-synthetic material.

8. The method of claim 1 wherein the strip is made of a tape material.

9. The method of claim 1 wherein a fastening means is attached to each opposing end of the strip of material.

* * * * *